(12) United States Patent
Aebersold et al.

(10) Patent No.: US 7,794,947 B2
(45) Date of Patent: Sep. 14, 2010

(54) AFFINITY CAPTURE OF PEPTIDES BY MICROARRAY AND RELATED METHODS

(75) Inventors: Rudolf H. Aebersold, Zürich (CH); Hui Zhang, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 0 days.

(21) Appl. No.: 10/888,084

(22) Filed: Jul. 9, 2004

(65) Prior Publication Data

US 2005/0095649 A1 May 5, 2005

Related U.S. Application Data

(60) Provisional application No. 60/486,581, filed on Jul. 10, 2003.

(51) Int. Cl.
G01N 33/53 (2006.01)
(52) U.S. Cl. ........................................ 435/7.1; 436/518
(58) Field of Classification Search ..................... 435/4, 435/7.1, 23, 29, 34, 68.1, 7.2, 7.91, 7.92; 436/501, 518, 811, 516
See application file for complete search history.

(56) References Cited

U.S. PATENT DOCUMENTS

| | | | | |
|---|---|---|---|---|
| 6,117,650 | A * | 9/2000 | King | 435/29 |
| 6,475,809 | B1 * | 11/2002 | Wagner et al. | 436/518 |
| 7,015,004 | B2 * | 3/2006 | Jackowski et al. | 435/7.1 |
| 7,052,916 | B2 * | 5/2006 | Johnson | 436/86 |
| 7,276,590 | B1 * | 10/2007 | Staby | 530/412 |
| 2002/0055186 | A1 | 5/2002 | Barry et al. | |
| 2002/0115056 | A1 | 8/2002 | Goodlett | |
| 2002/0168644 | A1 | 11/2002 | Aebersold et al. | |
| 2004/0023306 | A1 | 2/2004 | Aebersold et al. | |
| 2004/0033625 | A1 | 2/2004 | Aebersold et al. | |
| 2004/0038319 | A1 | 2/2004 | Aebersold et al. | |
| 2006/0008851 | A1 | 1/2006 | Aebersold et al. | |

FOREIGN PATENT DOCUMENTS

WO    WO 00/11208    3/2000
WO    WO 2004/031730 A2    4/2004

OTHER PUBLICATIONS

Fang et al, Molecular aptamer for real-time oncoprotein platelet derived growth factor monitoring by fluorescence anisotropy, 2001, Anal Chem, 73, 5752-5757.*
Griffen et al., Quantitative proteomic analysis using a MALDI quadrupole time-of-flight mass spectrometer, 2001, Anal Chem, 73, 978-986.*
Aebersold and Goodlett, "Mass spectrometry in proteomics," *Chem Rev.* 101:269-295 (2001).
Aebersold and Mann, "Mass spectrometry-based proteomics," *Nature* 422: 198-207 (2003).
Gerber et al., "Absolute quantification of proteins and phosphoproteins from cell lysates by tandem MS," *Proc. Natl. Acad. Sci. USA* 100:6940-6945 (2003).
Gygi et al., "Quantitative analysis of complex protein mixtures using isotope-coded affinity tags" *Nat. Biotechnol.* 17:994-999 (1999).
Yates, "Mass spectrometry and the age of the proteome" *J. Mass Spectrom.* 33:1-19 (1998).
Zhang et al., "Identification and quantification of N-linked glycoproteins using hydrazide chemistry, stable isotope labeling and mass spectrometry" *Nat. Biotechnol.* 21:660-666 (2003).
Zhou et al., "A systematic approach to the analysis of protein phosphorylation," *Nat. Biotechnol.* 19:375-378 (2001).
Zhou et al., "Quantitative proteome analysis by solid-phase isotope tagging and mass spectrometry" *Nat. Biotechnol.* 19:512-515 (2002).

* cited by examiner

*Primary Examiner*—Jacob Cheu
(74) *Attorney, Agent, or Firm*—McDermott Will & Emery LLP

(57) ABSTRACT

The invention provides methods of detecting polypeptides in a sample. The method can include the steps of cleaving polypeptides in a test sample to generate peptides; adding a predetermined amount of isotopically labeled peptide standards to the cleaved test sample, wherein the peptide standards correspond to peptides cleaved with the same reagent used to cleave the test sample; contacting the cleaved test sample containing peptide standards with an array of immobilized binding agents specific for the peptide standards; washing the array to remove unbound peptides, thereby retaining affinity captured sample peptides and standard peptides; analyzing the affinity captured peptides using mass spectrometry; and determining the presence of bound test peptides and standard peptides. The method can further include the step of quantifying the amount of the test peptides by comparing the ratio of test peptide to corresponding standard peptide.

44 Claims, 5 Drawing Sheets

MS scanning for spiked peptide mass

Spiking stable isotope-labeled peptide: VVGVPYQGDATALFILPSEGK

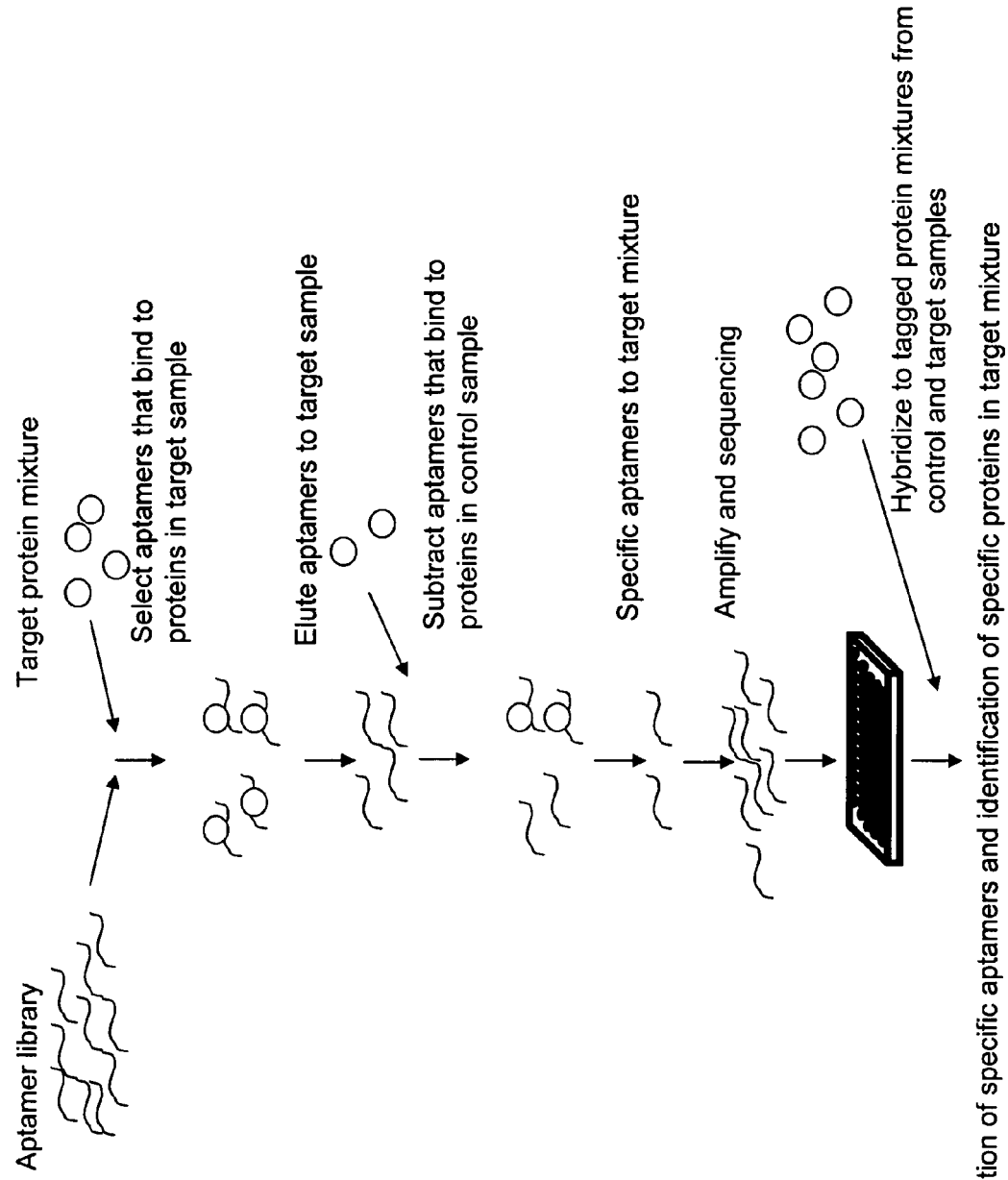

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Examplary peptide

<400> SEQUENCE: 1

Val Val Gly Val Pro Tyr Gln Gly Asp Ala Thr Ala Leu Phe Ile Leu
 1               5                  10                  15

Pro Ser Glu Gly Lys
            20
```

AFFINITY CAPTURE OF PEPTIDES BY MICROARRAY AND RELATED METHODS

This application claims the benefit of priority of U.S. provisional application Ser. No. 60/486,581, filed Jul. 10, 2003, the entire contents of which is incorporated herein by reference.

A number of approaches have been used to address the needs of proteomics analysis. For example, the combination of two-dimensional gel electrophoresis (2DE) and protein identification by mass spectrometry (MS) or tandem MS (MS/MS) constitute such a method. However, a limitation to this approach is that 2DE-MS analysis does not provide a true representation of the proteins in a biological sample because specific classes of proteins are known to be absent or under represented in 2D gel patterns. These include very acidic or basic proteins, excessively large or small proteins, membrane proteins and other proteins of poor solubility in aqueous solvents, and low abundance proteins.

Other methods for proteome analysis include quantitative mass spectrometry based on multidimensional peptide separation and isotope coded affinity tagging of proteins. This method allows relative quantification, that is, the determination of the abundance ratio of each protein in two samples but does not allow determination of the absolute quantity of the proteins in a sample. Another issue relates to the difficulties of analyzing complex mixtures, in particular the analysis of less abundant proteins in complex mixtures.

Thus, there exists a need for methods of high throughput and quantitative proteomic analysis of complex samples. The present invention satisfies this need and provides related advantages as well.

SUMMARY OF INVENTION

The invention provides methods of detecting polypeptides in a sample. The method can include the steps of cleaving polypeptides in a test sample to generate peptides; adding a predetermined amount of isotopically labeled peptide standards to the cleaved test sample, wherein the peptide standards correspond to peptides cleaved with the same reagent used to cleave the test sample; contacting the cleaved test sample containing peptide standards with an array of immobilized binding agents specific for the peptide standards; washing the array to remove unbound peptides, thereby retaining affinity captured sample peptides and standard peptides; analyzing the affinity captured peptides using mass spectrometry; and determining the presence of bound test peptides and standard peptides. The method can further include the step of quantifying the amount of the test peptides by comparing the ratio of test peptide to corresponding standard peptide.

BRIEF DESCRIPTION OF THE DRAWINGS

FIG. 5 shows the procedure to select and use aptamers specific to a target sample.

DETAILED DESCRIPTION OF THE INVENTION

Figure 1:
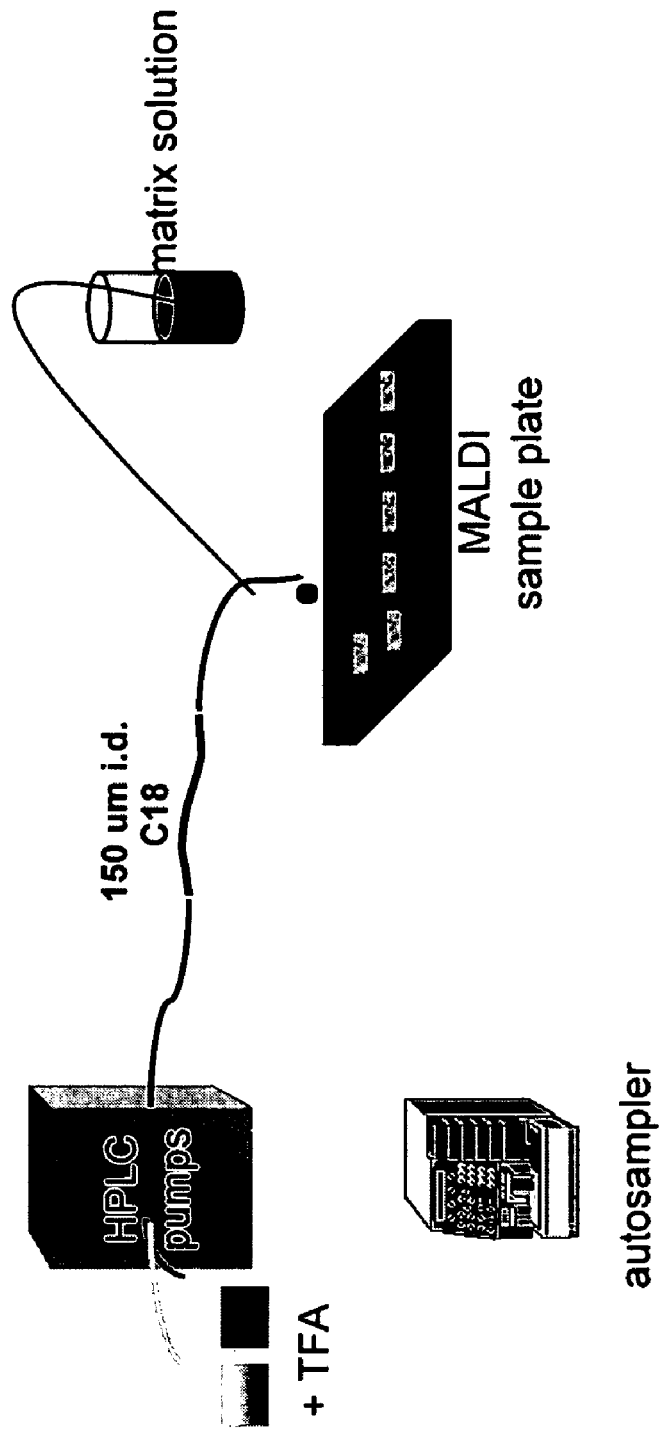
FIG. 1 shows complex mixture analysis by LC-MALDI mass spectrometry. A complex sample is separated by HPLC, exemplified using a C18 column. Fractions are spotted onto a MALDI sample plate for MS analysis.

The invention provides methods for rapid and high throughput analysis of proteins in complex samples. The methods are based on affinity capturing selected peptides and making a qualitative and/or quantitative analysis of peptides in a sample. The methods are advantageous in that a large number of proteins can be analyzed from complex mixtures. The use of binding agents increases the sensitivity for detecting proteins, especially low abundance proteins.

The detection and quantification of proteins and peptides in complex samples (quantitative proteomics) play a critical role in functional analysis of biological systems, the detection of clinical diagnostic or prognostic marker proteins, the identification of therapeutic targets, and the development of therapeutic agents. Since biological processes are controlled and executed by networks of interacting molecules, the concurrent detection, identification and quantification of a multitude of proteins and the availability of the bioinformatic tools to identify and analyze patterns of concurrently regulated proteins are important components of a systematic analysis of biological systems. Patterns of protein profiles are also expected to became useful for the early detection, diagnosis and prognosis of a multitude of diseases, including cancer, and for the identification of new drug targets and the development of optimal structures and dosages for pharmacological reagents. Currently, two main technical approaches are pursued to generate quantitative proteomic profiles. The first is based on mass spectrometry (MS) and the second is based on the use of ordered arrays of protein binding molecules. In the literature, the second technology is interchangeably referred to as protein chips, protein arrays, antibody arrays, and the like.

Mass spectrometry, at present, is the most mature technology for quantitative proteome profiling. Used in conjunction with stable isotope tagging of proteins, it has achieved the sensitivity, robustness and sample throughput that allow the identification and accurate quantification of a thousand proteins per day per mass spectrometry instrument if each target protein is identified, or approximately one thousand proteins per hour if quantitative patterns without identification are being generated. However, due to the "top down" mode of operation of mass spectrometry-based analysis, the most abundant proteins are preferentially or exclusively analyzed, and global proteome analyses will remain difficult, especially for the analysis of low abundant disease marker proteins. The top down problem is not really a problem of sensitivity of the mass spectrometer, nor is it strictly a problem of the dynamic range of the mass spectrometer. The main cause of the problem is that protease digestion of a complex protein mixture generates a peptide sample of enormous complexity. If that sample is injected into the MS system, the instrument does not have sufficient time to sequentially analyze each peptide. The system simply does not get to the lower abundance peptides, even though they may be present at sufficient amounts to be sequenced. Another difficulty analyzing low abundance proteins in a complex protein mixture is due to the competition of ionization, in which the high abundance peptides are preferentially ionized and detected by the mass spectrometer and the ionization of low abundant peptides is suppressed. This "ionization competition" is more profound in MALDI-based ionization method. To overcome these problems, several studies have adopted a "divide and conquer" strategy by comprehensively analyzing specific subsets of the proteome that are selectively isolated. Such studies include the analysis of functional multiprotein complexes or proteins that contain common distinguishing structural features, such as phosphate ester groups, cysteine residues or have the ability to specifically bind to certain compounds prior to MS analysis. These strategies have in common that they focus on the in-depth (ideally complete) analysis of proteins present even at a low abundance. Therefore, a general strategy for the selective isolation of specific proteins or classes of proteins would be of great advantage for mass spectrometry based quantitative proteomics.

The use of ordered arrays of specific probes has been highly successful for the generation of comprehensive, quantitative datasets. Initially pioneered in the context of mRNA expression analysis, the basic idea of ordered array analysis has been extended to also generate quantitative proteomic data. Strengths of the ordered array concept include high sample throughput, analysis of large numbers of samples in a single parallel operation, potentially low cost, potentially high reproducibility, and the like. Initial attempts to generate ordered arrays for quantitative proteomics have focused on the generation of antibody arrays in which antibodies specific for particular proteins are covalently immobilized on a solid phase through free primary amino groups. Detection of specific signals on antibody arrays has been based either on direct fluorescent labeling of antigens or sandwich assays using secondary antibodies. As alternative binding reagents, nucleotide aptamers, single chain Fv antibodies, minibodies and similar structures have been used as well. Among these, aptamer arrays are particularly appealing because the binding reagent itself is not proteinaceous. Aptamers are single-stranded nucleotide molecules that have the ability to bind their cognate proteins. Aptamers can be synthesized with an amine on the 5' terminus to provide a covalent anchor to an array surface. Currently, the detection of aptamer bound proteins is based on protein staining reagent such as NHS-Alexa555 or other amine-specific reagents coupled to enzymatic or fluorescent probes to label the lysines on the proteins.

Because of the nature of the binding reagent, the development of such arrays faces a number of significant challenges. First, it is the problem of "non-specific binding." For each binder (that is, array element), the conditions to achieve maximal discrimination between the specifically and non-specifically binding proteins may be different. Development of optimal binding and washing conditions for a whole array is therefore challenging. Second, many antibodies, and possibly also other binding reagents, show a significant degree of cross reactivity with proteins other than the intended target, thus complicating the detection of specific patterns. Third, each antibody, and likely also other binding reagents, has a different binding constant for the target protein and will establish equilibrium between bound and nonbound state on the chip, complicating quantification. Fourth, specific interactions require that the target proteins remain in solution. It is difficult to find conditions at which all target proteins are soluble and the specificity of the interactions remains intact. Therefore, a generic technology for quantitative proteomics based on arrays of protein binding reagents seems difficult to achieve.

Disclosed herein is a technology for quantitative proteomics that combines the strengths of array based and mass spectrometry based methods. Ordered arrays of reagents are generated that recognize peptides with a certain degree of specificity, the arrays are incubated with a sample solution containing the target peptides as well as other peptides, and the sequence and the quantity of the immobilized peptides are determined using mass spectrometry. The method takes advantage of the fast and parallel sample preparation of the array technologies, and the high specificity, accuracy and sensitivity of mass spectrometry. Specifically, antibody, aptamer or other affinity capture reagents are used for specific isolation and enrichment of interesting peptides. Known amounts of heavy isotope labeled target peptides are spiked into the biological sample to detect the presence and quantify the peptides.

The detection and quantification process can be described as the following steps:

1. Specific peptides of proteins from biological samples are identified.
2. The identified peptides or tryptic fragments of interesting proteins are synthesized with a heavy isotope incorporated at one fixed amino acid in the peptide sequence.
3. The synthetic peptides are used to produce antibodies or aptamers.
4. The antibodies or aptamers are immobilized on a solid support to make microarrays.
5. Proteins from cells or body fluids are digested by trypsin, and the trypsin is removed from peptides.
6. Known amounts of heavy isotope coded peptides are spiked to the peptides from biological samples.
7. The microarrays are incubated with a binding solution containing tryptic peptides from step 5 and 6. Specific peptides are captured by antibodies or aptamers on microarray.
8. Microarrays are washed to remove nonspecifically bound protein.
9. MALDI matrix is added to each spot and the affinity captured peptides are detected by mass spectrometry.
10. The presence of light isotope peptides and the ratio of biological light and in vitro added heavy isotope tagged peptides are determined.

This is a high throughput, sensitive, and specific method for quantitative proteomic analysis. The technique has the following advantages. i) The specificity of the binding reagents allows for the enrichment of particular analytes so that they can be detected even if they are present below the concentration detection limit of the mass spectrometer. ii) The dual specificity provided by the selection reagent and the mass spectrometer provides the possibility of detecting selected analytes in very complex samples. iii) The solubility issues associated with protein arrays are eliminated as the more soluble peptides are being detected. iv) In the process, multiple parallel samples can be prepared and analyzed by a single high throughput mass spectrometer. v) Splice isoforms, modified peptides, and differentially processed peptides can be identified and quantified, provided that the targeted peptide can be synthesized. vi) The method is very sensitive. The antibodies or aptamers to each peptide can specifically capture the specific peptide to a certain spot and remove other peptides from the analysis, thus increasing sensitivity of the analysis. In addition, because the mass of peptide in each spot is known, the mass spectrometer can focus on only the scanning of the known mass window and increase the sensitivity 10 to 100 fold.

The technology is useful for the analysis of complex protein expression patterns associated with a disease, for the rapid generation of quantitative protein expression profiles without the need for chromatographic separation of the analytes, and for monitoring the specificity and efficacy of drugs. Multiple proteins are changed during disease. The miniaturized microarray platform and use of mass spectrometry as detection method can efficiently detect and quantify hundreds of proteins simultaneously. The detection of known mass of each peptide in each spot eliminates the detection of non-specific binding of other peptides from the analysis and increases the specificity and accuracy of quantification. The introducing of heavy isotope tagged peptides in the analysis increases the accuracy of quantification and serves as a positive control for detecting the presence of the light isotope form of a peptide from a biological sample. This differentiates the real biological variation from the experimental variation and increases the confidence of the results.

The invention provides a method of detecting polypeptides in a sample. The method can include the steps of identifying a set of peptides corresponding to polypeptides of interest in a sample; synthesizing isotopically labeled forms of the set of peptides to generate peptide standards; generating a plurality of binding agents for the set of peptides; immobilizing the plurality of binding agents to a solid support in an array format; cleaving polypeptides in a test sample to generate peptides corresponding to the peptide standards; adding a predetermined amount of the peptide standards to the cleaved test sample; contacting the cleaved test sample containing peptide standards with the array of immobilized binding agents; washing the array to remove unbound peptides, thereby retaining affinity captured sample peptides and standard peptides; analyzing the affinity captured peptides using mass spectrometry; determining the presence of bound test peptides and standard peptides; and quantifying the amount of the test peptides by comparing the ratio of test peptide to corresponding standard peptide.

As used herein, the term "polypeptide" refers to a peptide or polypeptide of two or more amino acids. A polypeptide can also be modified by naturally occurring modifications such as post-translational modifications, including phosphorylation, fatty acylation, prenylation, sulfation, hydroxylation, acetylation, addition of carbohydrate, addition of prosthetic groups or cofactors, formation of disulfide bonds, proteolysis, assembly into macromolecular complexes, and the like.

As used herein, the term "sample" is intended to mean a biological fluid, cell, tissue, organ or portion thereof, that includes one or more different molecules such as nucleic acids, polypeptides, or small molecules. A sample can be a tissue section obtained by biopsy, or cells that are placed in or adapted to tissue culture. A sample can also be a biological fluid specimen such as blood, plasma or serum, cerebrospinal fluid, urine, saliva, seminal plasma, pancreatic juice, and the like. A sample can additionally be a cell extract from any species, including prokaryotic and eukaryotic cells as well as viruses. A tissue or biological fluid specimen can be further fractionated, if desired, to a fraction containing particular cell types.

As used herein, a "polypeptide sample" refers to a sample containing two or more different polypeptides. A polypeptide sample can include tens, hundreds, or even thousands or more different polypeptides. A polypeptide sample can also include non-protein molecules so long as the sample contains polypeptides. A polypeptide sample can be a whole cell or tissue extract or can be a biological fluid. Furthermore, a polypeptide sample can be fractionated using well known methods, as disclosed herein, into partially or substantially purified protein fractions.

The use of biological fluids such as a body fluid as a sample source is particularly useful in methods of the invention. Biological fluid specimens are generally readily accessible and available in relatively large quantities for clinical analysis. Biological fluids can be used to analyze diagnostic and prognostic markers for various diseases.

The methods of the invention can be used to determine the presence of polypeptides of interest in a sample. The methods are particularly useful for diagnostic purposes. Polypeptides in a sample to be tested can be selected based on desired criteria, for example, polypeptides known to be present in a particular sample or expressed in a disease state. Once desired polypeptides representative of the sample are selected, peptides derived from the polypeptides are selected using desired criteria. For example, peptides can be selected based on theoretical digests using a particular protease such as trypsin. One or more peptides derived from the polypeptides can be selected as representative of the polypeptides.

Once a set of peptides corresponding to polypeptides of interest are identified, the peptides are synthesized in a heavy isotope form to be used as a standard for MS analysis. Standard peptides are selected to analyze a desired set of polypeptides. The amount of standard peptides to be added can be adjusted, as desired, to facilitate quantification, and each of the peptide standards added need not be in the same amounts.

The peptide sequences to be used as standards, once selected, are chemically synthesized by solid-phase stepwise synthesis, and in one embodiment are synthesized incorporating a heavy amino acid, and quantified. Methods of synthesizing peptides are well known to those skilled in the art (Merrifield, *J. Am. Chem. Soc.* 85:2149 (1964); Bodanszky, M., *Principles of Peptide Synthesis* (Springer-Verlag, 1984); Houghten, *Proc. Natl. Acad. Sci. USA* 82:5131 (1985)). For each peptide, a calibrated sample stock solution can be prepared and stored. Quantification of the calibrated stock solution can be carried out by amino acid composition analysis, can be based on UV absorbance measurement or other spectrometric methods, or by weighing the dried peptide.

Alternatively, the standard peptides can be generated by expression in a genetically engineered organism such as *Escherichia coli* or other microorganisms. Each peptide can be expressed separately as a peptide product, as part of a larger polypeptide from which the peptide will be cut out by proteolysis, or in the form of concatenated peptides, which can be resolved into individual peptide species by proteolysis or chemical cleavage at suitable sites. Once isolated, the peptides generated by genetic engineering and overexpression can be isotopically labeled, for example, using an isotope tag, and used in the methods of the invention, as with the chemically synthesized peptides. Alternatively, the microorganism can be grown in the presence of a heavy amino acid for incorporation into the standard peptide expressed recombinantly.

In another embodiment, the standard peptides are synthesized and labeled with an isotope tag. Isotope tagging of peptides is well known to those skilled in the art (see, for example, Gygi et al., *Nat. Biotechnol.* 17:994-999 (1999); WO 00/11208; U.S. publication 2004/0033625; U.S. publication 2004/0038319, each of which is incorporated herein by reference). An isotope tag refers to a chemical moiety having suitable chemical properties for incorporation of an isotope, allowing the generation of differentially labeled reagents which can be used to differentially tag peptides. The isotope tag also has an appropriate composition to allow incorporation of a stable isotope at one or more atoms. A particularly useful stable isotope pair is hydrogen and deuterium, which can be readily distinguished using mass spectrometry as light and heavy forms, respectively. Any of a number of isotopic atoms can be incorporated into the isotope tag so long as the heavy and light forms can be distinguished using mass spectrometry, for example, $^{13}C$, $^{15}N$, $^{17}O$, $^{18}O$ or $^{34}S$. Exemplary isotope tags include the 4,7,10-trioxa-1,13-tridecanediamine based linker and its related deuterated form, 2,2',3,3',11,11', 12,12'-octadeutero-4,7,10-trioxa-1,13-tridecanediamine, described by Gygi et al. (*Nature Biotechnol.* 17:994-999 (1999). Other exemplary isotope tags have also been described previously (see WO 00/11208). In contrast to these previously described isotope tags related to an ICAT™-type reagent, it is not required that an affinity tag be included in the reagent since the peptides are to be isolated with binding agents in methods of the invention. One skilled in the art can readily determine any of a number of appropriate isotope tags useful in methods of the invention. It is understood that when sample and standard peptides are differentially isotopically labeled with an isotope tag, the standard peptides can be labeled with either heavy and light forms of the isotope tag so long as the sample peptides are labeled with the other form so that the standard and sample peptides are differentially labeled.

An isotope tag can be an alkyl, alkenyl, alkynyl, alkoxy, aryl, and the like, and can be optionally substituted, for example, with O, S, N, and the like, and can contain an amine, carboxyl, sulfhydryl, and the like (see WO 00/11208). These and other derivatives can be made in the same manner as that disclosed herein using methods well known to those skilled in the art. One skilled in the art will readily recognize that a number of suitable chemical groups can be used as an isotope tag so long as the isotope tag can be differentially isotopically labeled. The stable isotope tag can also be introduced via a solid-phase stable isotope tag transfer method, such as the one described by Zhou et al., *Nature Biotechnol.* 20:512-515 (2002).

The peptide fragments are tagged with an isotope tag to facilitate MS analysis. In order to tag the peptide fragments, the isotope tag contains a reactive group that can react with a chemical group on the peptide portion of the peptide fragments. A reactive group is reactive with and therefore can be covalently coupled to a molecule in a sample such as a polypeptide. Reactive groups are well known to those skilled in the art (see, for example, Hermanson, *Bioconjugate Techniques*, pp. 297-364, Academic Press, San Diego (1996); Glazer et al., *Laboratory Techniques in Biochemistry and Molecular Biology: Chemical Modification of Proteins*, Chapter 3, pp. 68-120, Elsevier Biomedical Press, New York (1975); Pierce Catalog (1994), Pierce, Rockford Ill.). Any of a variety of reactive groups can be incorporated into an isotope tag for use in methods of the invention so long as the reactive group can be covalently coupled to a polypeptide or other desired molecule in a sample. For example, a polypeptide can be coupled via a sulfhydryl reactive group, which can react with free sulfhydryls of cysteine or reduced cystines in a polypeptide. An exemplary sulfhydryl reactive group includes an iodoacetamido group (see Gygi et al., supra, 1999). Other examplary sulfhydryl reactive groups include maleimides, alkyl and aryl halides, haloacetyls, α-haloacyls, pyridyl disulfides, aziridines, acrylolyls, arylating agents and thiomethylsulfones.

A reactive group can also react with amines such as the α-amino group of a peptide or the ε-amino group of the side chain of Lys, for example, imidoesters, N-hydroxysuccinimidyl esters (NHS), isothiocyanates, isocyanates, acyl azides, sulfonyl chlorides, aldehydes, ketones, glyoxals, epoxides (oxiranes), carbonates, arylating agents, carbodiimides, anhydrides, and the like. A reactive group can also react with carboxyl groups found in Asp or Glu or the C-terminus of a peptide, for example, diazoalkanes, diazoacetyls, carbonyldiimidazole, carbodiimides, and the like. A reactive group that reacts with a hydroxyl group includes, for example, epoxides, oxiranes, carbonyldiimidazoles, N,N'-disuccinimidyl carbonates, N-hydroxycuccinimidyl chloroformates, and the like. A reactive group can also react with amino acids such as histidine, for example, α-haloacids and amides; tyrosine, for example, nitration and iodination; arginine, for example, butanedione, phenylglyoxal, and nitromalondialdehyde; methionine, for example, iodoacetic acid and iodoacetamide; and tryptophan, for example, 2-(2-nitrophenylsulfenyl)-3-methyl-3-bromoindolenine (BNPS-skatole), N-bromosuccinimide, formylation, and sulfenylation (Glazer et al., supra, 1975). In addition, a reactive group can also react with a phosphate group for selective labeling of phosphopeptides (Zhou et al., *Nat. Biotechnol.*, 19:375-378 (2001)), or with other covalently modified peptides, including lipopeptides, or any of the known covalent polypeptide modifications. One skilled in the art can readily determine conditions for modifying sample molecules or standard peptides by using various reagents, incubation conditions and time of incubation to obtain conditions optimized for modification with an isotope tag. The use of covalent-chemistry based isolation methods is particularly useful due to the highly specific nature of the binding of the polypeptides.

The reactive groups described above can form a covalent bond with the target sample molecule. However, it is understood that an isotope tag can contain a reactive group that can non-covalently interact with a sample molecule so long as the interaction has high specificity and affinity.

Once a set of peptides is selected as a standard for representation of desired polypeptides, a plurality of binding agents is generated for each of the peptides. Exemplary binding agents include antibodies, aptamers, or other suitable affinity capture reagents for isolation and enrichment of peptides of interest. If desired, peptides used to generate binding agents such as antibodies or aptamers can be synthesized with a linker, for example, a particular amino acid or chemical group suitable for coupling to a carrier or solid support.

Methods for preparing antibodies are well known to those skilled in the art. As used herein, the term "antibody" is used in its broadest sense to include polyclonal and monoclonal antibodies, as well as antigen binding fragments of such antibodies. An antibody useful in the invention, or antigen binding fragment of such an antibody, is characterized by having specific binding activity for a polypeptide or a peptide portion thereof of at least about $1 \times 10^5 M^{-1}$. Thus, Fab, F(ab')$_2$, Fd, Fv, single chain Fv (scFv) fragments of an antibody and the like, which retain specific binding activity for a polypeptide, are included within the definition of an antibody, as well as minibodies. Specific binding activity of an antibody for a polypeptide can be readily determined by one skilled in the art, for example, by comparing the binding activity of an antibody to a particular peptide versus a control peptide that is not the particular peptide. Methods of preparing polyclonal or monoclonal antibodies and anti-peptide antibodies are well known to those skilled in the art (see, for example, Harlow and Lane, *Antibodies: A Laboratory Manual*, Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989)). These and other methods of making functional antibodies are well known to those skilled in the art (Winter and Harris, *Immunol. Today* 14:243-246 (1993); Ward et al., *Nature* 341:544-546 (1989); Harlow and Lane, supra, 1988); Hilyard et al., *Protein Engineering: A practical approach* (IRL Press 1992); Borrabeck, *Antibody Engineering*, 2d ed. (Oxford University Press 1995)).

Methods of preparing aptamers are also well known to those skilled in the art. Aptamers are oligonucleotides having binding affinity for polypeptides (Tuerk and Gold, *Science* 249:505-510 (1990); Ellington and Szostak, *Nature* 346:818-822 (1990); Joyce, *Curr. Otpin. Struct. Biol.* 4:331-336 (1994); Gold et al., *Annu. Rev. Biochem.* 64:763-797 (1995); Jayasena, *Clin. Chem.* 45:1628-1650 (1999); Famulok and Mayer, *Curr. Top. Microbiol. Immunol.* 243:123-136 (1999)). A diversity of at least $10^{15}$ species can be synthesized. For example, DNA apatmers can be synthesized with variable nucleic acid sequences flanked on each end by recognition sites for PCR primers. If desired, apatamers that bind to a peptide can be selected and amplified, and such apatmers can have affinities greater than antibodies.

Once a plurality of binding agents is generated for the selected peptides, the binding agents are immobilized to a solid support. Methods of coupling binding agents to a solid support are well known to those skilled in the art (see, for example, Hermanson, *Bioconjugate Techniques* Academic Press, San Diego (1996)). If desired, the solid support can be in the format of an array, such as a microarray. Methods of coupling antibodies or nucleic acids such as aptamers to an array are well known to those skilled in the art. An array format is convenient for analyzing a relative large number of peptides rather than just a few peptides.

Figure 3:
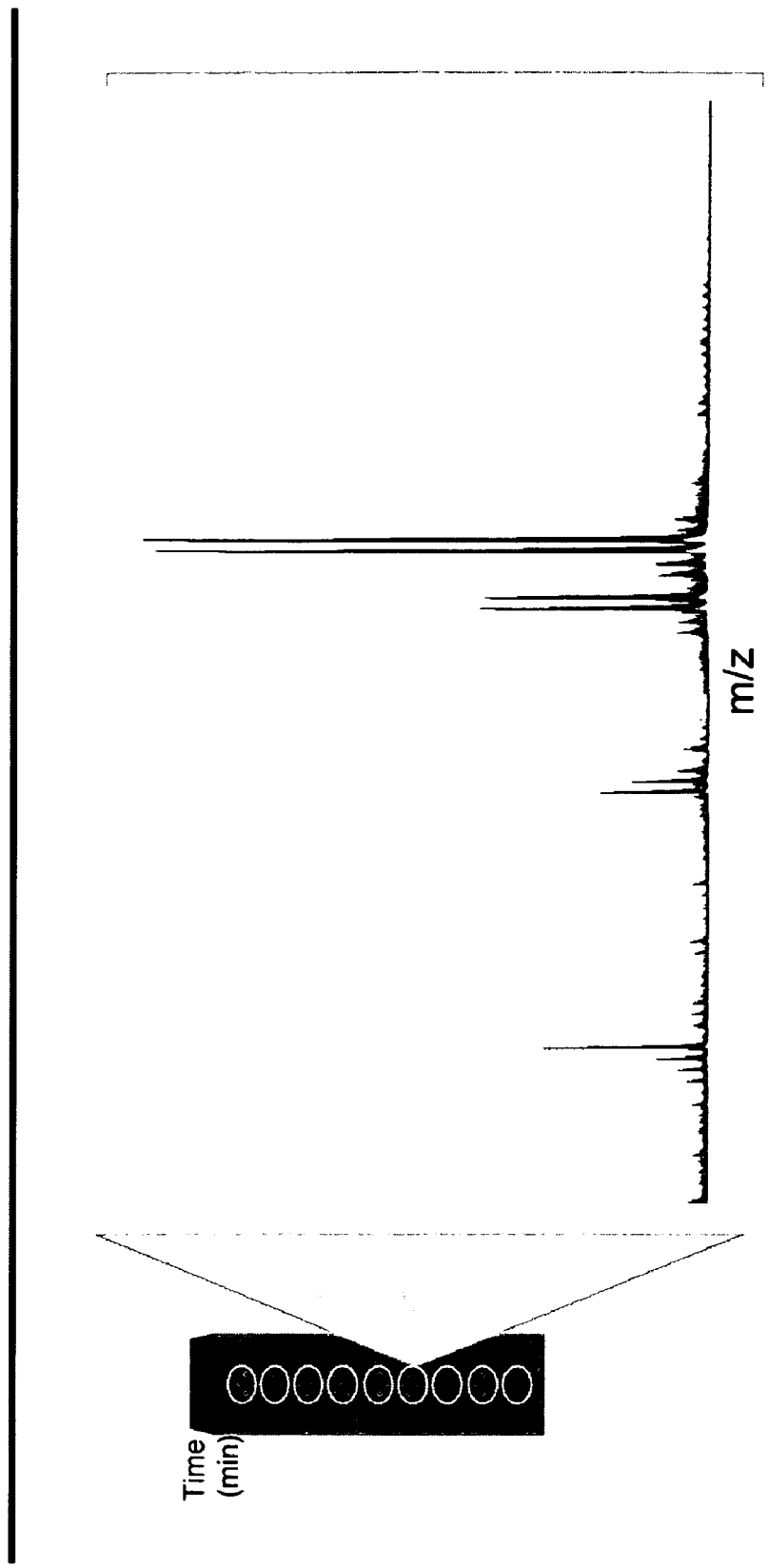
FIG. 3 depicts mass spectrometry scanning for spiked peptide mass.

Sample polypeptides are cleaved with a reagent that generates the same peptide sequence as the peptide standards. For example, if the peptide standards are based on tryptic digests, then trypsin is used to cleave polypeptides in the sample. It is understood that, in methods of the invention, the cleavage method used for the sample will correspond to the cleavage method used to derive the standard peptides. It is further understood that the peptide standards that correspond to a particular cleavage method can be derived by cleavage with the respective reagent or synthesized so that the resulting peptide is identical to a peptide cleaved with the respective reagent. This results in the standard and test peptides differing only by the isotopic label, which means that the standard and test peptides can be detected with a predicted mass difference in the mass spectrometer (see FIG. 3). A polypeptide molecule can be enzymatically cleaved with one or more proteases into peptide fragments. Exemplary proteases useful for cleaving polypeptides include trypsin, chyrnotrypsin, pepsin, papain, *Staphylococcus aureus* (V8) protease, Submaxillaris protease, bromelain, thermolysin, and the like. Polypeptides can also be cleaved chemically, for example, using CNBr, acid or other chemical reagents, so long as the cleavage method results in peptides corresponding to the standard peptides. If desired, the polypeptides in the sample can be denatured and optionally reduced.

After cleavage of the sample polypeptides, the cleavage reagent can optionally be removed. Removal of the cleavage reagent is desirable if the reagent can cleave the binding agents to which the cleaved sample peptides will be subsequently bound. For example, if a protease is used as the cleavage reagent and the binding agent is a protein such as an antibody, then it is desirable to remove the protease prior to binding the digested sample to the binding agents. However, if the binding agent is not a protein, for example, is an aptamer, then it is not necessary to remove the cleavage reagent, although it can be performed. Methods of removing a cleavage reagent are well known to those skilled in the art, for example, using a protease bound to a solid support, which can be readily removed after the cleavage reaction, or using affinity chromatography or other types of chromatography to remove the cleavage reagent.

A predetermined amount of peptide standards is added to the sample, either before or after digestion with the corresponding cleavage reagent. One skilled in the art can readily select an appropriate amount of each peptide to add, in particular to facilitate quantification. It is understood that the same amount of each peptide need not be added. In general, the amount of peptide to be added is in a range suitable for quantification and can be adjusted to be optimized for the amount of peptide found in a given sample. For example, the amount of a given peptide in a sample can be calibrated by adding various known amounts of a standard peptide to determine an appropriate range for detection in the mass spectrometer.

The cleaved test sample, to which standard peptides have been added, is contacted with a plurality of immobilized binding agents. The binding agents can be immobilized, for example, on an array such as a microarray. The binding agents can be arranged on the array in predetermined locations to facilitate identification of the peptides and subsequent analysis by MS. The sample is incubated for an amount of time sufficient for binding of the peptides to their respective binding agents. One skilled in the art can readily determine a suitable amount of time to allow binding of peptides to the binding agents.

Once the binding reaction has occurred, the unbound material is removed and the solid support is washed to remove non-specifically bound material. One skilled in the art can readily determine suitable wash conditions to remove non-specifically bound material while retaining specifically bound peptides. Suitable buffers are chosen for washing and can contain salts, detergents, or other agents that remove non-specifically bound material while retaining specifically bound peptides.

The peptides bound to the solid support, which includes both sample peptides and standard peptides, are analyzed by mass spectrometry. A variety of mass spectrometry systems can be employed in the methods of the invention for identifying and/or quantifying a sample molecule such as a polypeptide. Mass analyzers with high mass accuracy, high sensitivity and high resolution include, but are not limited to, triple quadrupole, time-of-flight, quadrupole time-of-flight mass spectrometers, and Fourier transform ion cyclotron mass analyzers (FT-ICR-MS). Mass spectrometers are typically equipped with matrix-assisted laser desorption (MALDI) or electrospray ionization (ESI) ion sources, although other methods of peptide ionization can also be used. In MS analyses, analytes are ionized by electrospray ionization or MALDI and then put into a mass analyzer. Sample molecules can be analyzed, for example, by single stage mass spectrometry with a MALDI-TOF or ESI-TOF system. Methods of mass spectrometry analysis are well known to those skilled in the art (see, for example, Yates, *J. Mass Spect.* 33:1-19 (1998); Kinter and Sherman, *Protein Sequencing and Identification Using Tandem Mass Spectrometry*, John Wiley & Sons, New York (2000); Aebersold and Goodlett, *Chem. Rev.* 101:269-295 (2001); Aebersold and Mann, *Nature* 422:198-207 (2003)).

While mass spectrometers using MALDI ionization are particularly useful in methods of the invention, it is understood that mass spectrometers equipped with ion sources of different types are also applicable in the methods of the invention. Specifically, mass spectrometers equipped with ESI ion sources are also suitable for methods of the invention. These include electrospray ionization time-of-flight (ESI-TOF) mass spectrometers and ESI-qTOF, ion trap, triple quadrupole and FT-MS mass spectrometers.

The mass spectrometer is used to determine the presence of bound test peptides and standard peptides. The use of identical but isotopically distinct standard peptides allows a direct comparison of test and sample peptides. Methods of using isotopic labeling for quantification are well known to those skilled in the art (see, for example, Gygi et al., *Nat. Biotechnol.* 17:994-999 (1999); WO 00/11208; U.S. publication 2004/0033625). By adding in known amounts of standard peptides, the ratio of standard peptide versus sample peptide, as measured using the differential isotopic label, can be used to quantify the amount of sample peptide in the test sample.

The methods of the invention use selected peptide standards, which can be bound in a predetermined location on the array. Since the mass of the peptide and location on the array are both known, the mass spectrometer can be focused on scanning the known mass window at a particular location, thus increasing sensitivity of the analysis.

The invention additionally provides a method of detecting polypeptides in a sample by cleaving polypeptides in a test sample to generate peptides; adding a predetermined amount of isotopically labeled peptide standards to the cleaved test sample, wherein the peptide standards correspond to peptides cleaved with the same reagent used to cleave the test sample; contacting the cleaved test sample containing peptide standards with an array of immobilized binding agents specific for the peptide standards; washing the array to remove unbound peptides, thereby retaining affinity captured sample peptides and standard peptides; analyzing the affinity captured peptides using mass spectrometry; determining the presence of bound test peptides and standard peptides; and optionally quantifying the amount of the test peptides by comparing the ratio of test peptide to corresponding standard peptide. The cleavage reagent can be, for example, trypsin. As used herein, peptide standards that correspond to peptides cleaved with the same reagent have the same sequence as the sample peptides cleaved with the same reagent, for example, tryptic peptide sequences for the sample and standard peptides. If a peptide of interest has a covalent modification, such as phosphorylation, glycosylation, or other post-translational modifications, then the peptide sequence and the covalent modification are the same between the sample peptide and test peptide and are therefore corresponding peptides.

The invention further provides a method of detecting polypeptides in a sample. The method can include the steps of cleaving polypeptides in a test sample with trypsin to generate peptides; adding a predetermined amount of isotopically labeled peptide standards to the cleaved test sample, wherein the peptide standards correspond to tryptic peptides; contacting the cleaved test sample containing peptide standards with an array of immobilized binding agents specific for the peptide standards; washing the array to remove unbound peptides, thereby retaining affinity captured sample peptides and standard peptides; analyzing the affinity captured peptides using mass spectrometry; and determining the presence of bound test peptides and standard peptides. The method can further include the step of quantifying the amount of the test peptides by comparing the ratio of test peptide to corresponding standard peptide.

As disclosed herein, the methods of the invention can be used to assess the presence of polypeptides in a complex biological sample. The advantage of using a body fluid as a biological sample is that it is readily accessible and requires minimal processing. If desired, however, the biological samples can be processed prior to analysis. For preparation of the protein samples, standard protocols are used to prepare and process the protein samples. Methods for preparing and processing protein samples are well known to those skilled in the art (Scopes, *Protein Purification: Principles and Practice*, third edition, Springer-Verlag, New York (1993)). If desired, the sample can be fractionated by a number of known fractionation techniques. Fractionation techniques can be applied at any of a number of suitable points in the methods of the invention. Thus, if desired, a substantially purified sample fraction can be used. One skilled in the art can readily determine appropriate steps for fractionating sample molecules based on the needs of the particular application of methods of the invention.

Fractionation methods include but are not limited to separation of cells or cell types in a sample, for example, separation of cells in blood or isolation of cell types in a tissue, subcellular fractionation or chromatographic techniques such as ion exchange, including strong and weak anion and cation exchange resins, hydrophobic and reverse phase, size exclusion, affinity, hydrophobic charge-induction chromatography, dye-binding, and the like (Ausubel et al., *Current Protocols in Molecular Biology* (Supplement 61), John Wiley & Sons, New York (2003); Scopes, *Protein Purification: Principles and Practice*, third edition, Springer-Verlag, New York (1993); Burton and Harding, *J. Chromatogr. A* 814:71-81 (1998)). Other fractionation methods include, for example, centrifugation, electrophoresis, the use of salts, and the like (see Scopes, supra, 1993). One skilled in the art will recognize that these and other fractionation methods, which are well known to those skilled in the art, can be used to fractionate polypeptides or peptides.

Affinity chromatography can also be used including, for example, dye-binding resins such as Cibacron blue, substrate analogs, including analogs of cofactors such as ATP, NAD, and the like, ligands and the like. Affinity chromatography can also be performed using DNA, lectins or other natural substances as an affinity ligand. The resolution and capacity of particular chromatographic media are known in the art and can be determined by those skilled in the art. The usefulness of a particular chromatographic separation for a particular application can similarly be assessed by those skilled in the art. In addition to fractionation methods, affinity chromatography steps are also used to select peptides from a complex mixture, for example, using antibodies, apatamers, or other affinity capture reagents.

Those of skill in the art will be able to determine the appropriate chromatography conditions for a particular sample size or composition and will know how to obtain reproducible results for chromatographic separations under defined buffer, column dimension, and flow rate conditions. The fractionation methods can optionally include the use of an internal standard for assessing the reproducibility of a particular chromatographic application or other fractionation method. Appropriate internal standards will vary depending on the chromatographic medium or the fractionation method used. Those skilled in the art will be able to determine an internal standard applicable to a method of fractionation such as chromatography.

Electrophoresis, including gel electrophoresis or capillary electrophoresis, can also be used to fractionate sample molecules. Electrophoresis techniques include but are not limited to isoelectric focusing (IEF), sodium dodecyl sulfate polyacrylamide gel electrophoresis (SDS-PAGE) or acid-urea gel electrophoresis. As discussed herein, sample molecules can be processed, for example, by protease cleavage into peptide fragments. Accordingly, when referring to sample molecules, the sample molecules can be intact as found in an original sample or can be processed, for example, into smaller molecules such as peptides from a polypeptide sample.

If desired, the sample can be processed so that a subset of polypeptides in the original sample is analyzed. For example, it is possible to isolate glycopolypeptides by specifically absorbing oxidized glycopolypeptides to a hydrazide resin (see, for example, Zhang et al., *Nat. Biotechnol.* 21:660-666 (2003); Aebersold and Zhang, U.S. publication 2004/0023306, each of which is incorporated herein by reference) (see Example 1). If desired, N-glycosylated peptides can be selectively analyzed by using an N-glycosidase to release glycopeptides bound to the hydrazide resin. Methods of isolating phosphoproteins are also well known to those skilled in the art and can be applied to isolate a subset of polypeptides that are phosphorylated (Zhou et al., *Nat. Biotechnol.* 19:375-378 (2001)).

The methods of the invention are also applicable to the identification and quantification of post-translational modifications. For analysis of polypeptides having post-translational modifications, a modified peptide having a known post-translational modification is chemically synthesized and used in the methods of the invention, as described above. Methods for the synthesis of phosphorylated peptides are well known to those skilled in the art, and other types of modifications readily can be synthesized by those skilled in the art (Gerber et al., *Proc. Natl. Acad. Sci. USA* 100:6940-6945 (2003)).

The methods of the invention can be used for diagnostic purposes. For example, the standard peptides selected for analysis can include peptides derived from proteins known to have altered expression in a particular disease state. The methods of the invention can be used to identify disease markers, for example, by comparing a control sample to a test sample such as a disease sample (see Example 3). In addition, a number of diagnostic markers for a particular disease state are well known to those skilled in the art. In addition, methods of identifying disease markers are well known to those skilled in the art (see, for example, U.S. publication 2004/0023306). By comparing disease and healthy samples, a diagnostic pattern can be determined with increases or decreases in expression of particular polypeptides correlated with the disease, which can be used for subsequent analysis of samples for diagnostic purposes.

The methods of the invention are applicable in clinical and diagnostic medicine, veterinary medicine, agriculture, and the like. For example, the methods of the invention can be used to identify and/or validate drug targets and to evaluate drug efficacy, drug dosing, optimization of drug leads, and/or drug toxicity. The methods of the invention can be used to look for changes in polypeptide profiles, for example, in serum or plasma, associated with drug administration and correlated with the effects of drug efficacy, dosing and/or toxicity, optimization of drug leads, and/or validation of drug targets. Such a correlation can be readily determined, for example, by collecting serum samples from one or more individuals administered various drug doses, experiencing drug toxicity, experiencing a desired efficacy, and the like. In addition, a serum profile can be generated in combination with the analysis of drug targets as a way to rapidly and efficiently validate a particular target with the administration of a drug or various drug doses, toxicity, and the like.

The invention also provides reagents and kits for identifying and quantifying polypeptides in a sample. The kit can contain, for example, a collection of isotopically labeled peptide standards. For example, the kit can contain a set of calibrated synthetic standard peptides of known relative or absolute amounts. The kit can also include a set of one or more isotope tags differentially labeled from that of the standard peptides for coupling to sample polypeptides, if the standard peptides are labeled with an isotope tag. The kit can also contain a protease(s) or other cleavage reagent corresponding to the cleavage method used to derive the peptide standards. The contents of the kit of the invention, for example, any standard peptides or labeling reagents, are contained in suitable packaging material, and, if desired, a sterile, contaminant-free environment. In addition, the packaging material can contain instructions indicating how the materials within the kit can be employed to label sample molecules. The instructions for use typically include a tangible expression describing the reagent concentration or at least one assay method parameter, such as the relative amounts of reagent and sample to be admixed and how to adjust the amounts if needed for quantification, maintenance time periods for reagent/sample admixtures, temperature, buffer conditions, and the like. The kits also can include an array of binding agents, such as aptamers or antibodies, that specifically bind to the standard peptides included in the kit.

It is understood that modifications which do not substantially affect the activity of the various embodiments of this invention are also provided within the definition of the invention provided herein. Accordingly, the following examples are intended to illustrate but not limit the present invention.

EXAMPLE 1

Quantitative Analysis of Peptides from a Complex Biological Sample

This example describes the analysis of cleaved test peptides and standard peptides from a complex biological sample by mass spectrometry.

FIG. 1 shows the analysis of a complex mixture using LC-MALDI MS. Sample peptides isolated from human serum using glycopeptide capture (similar to the methods described by Zhang et al., *Nat. Biotechnol.* 21:660-666 (2003); and Aebersold and Zhang, U.S. publication 2004/0023306) and heavy isotope labeled standard peptides were resolved on a C18 column and spotted on a MALDI sample plate for MS analysis.

Figure 2:
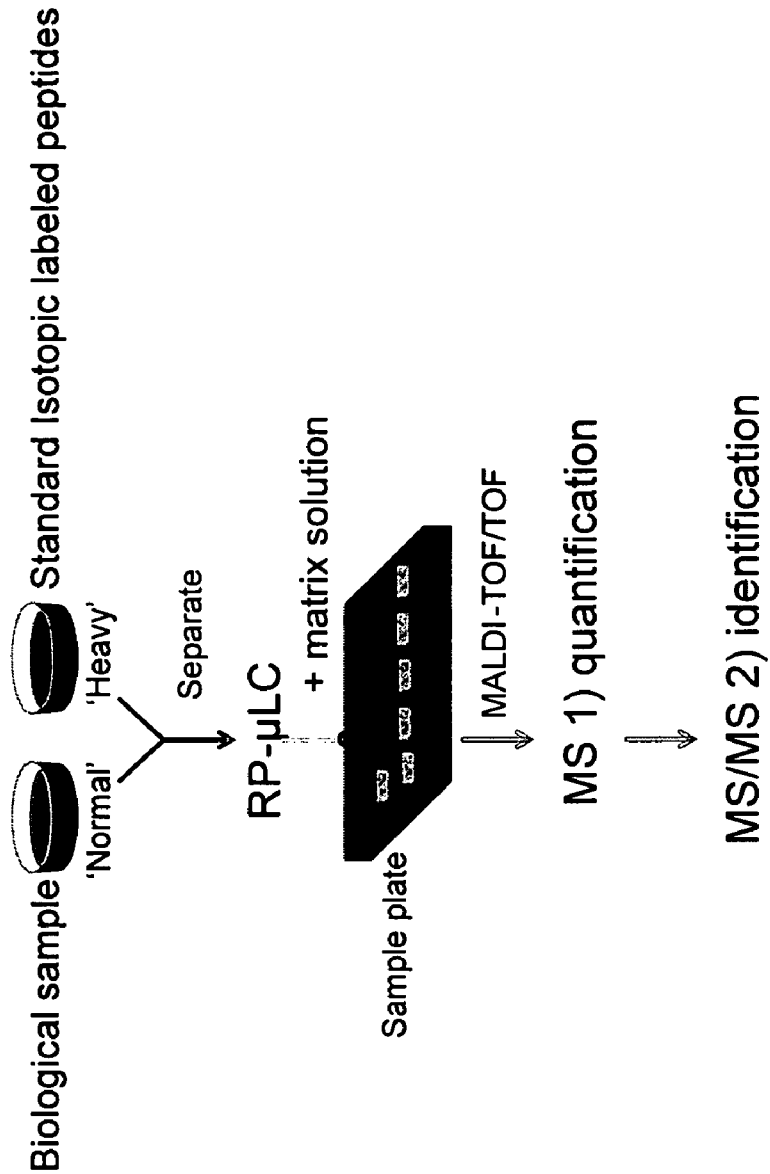
FIG. 2 shows quantitative analysis of serum proteins by MALDI-TOF/TOF. A biological sample is mixed with standard isotopic labeled peptides that correspond to the same cleavage method used for the biological sample, for example, cleavage with trypsin. Fractions are separated on a reverse phase column and spotted on a MALDI sample plate. The samples are analyzed by MALDI-TOF/TOF for quantification and identification.
Figure 4:
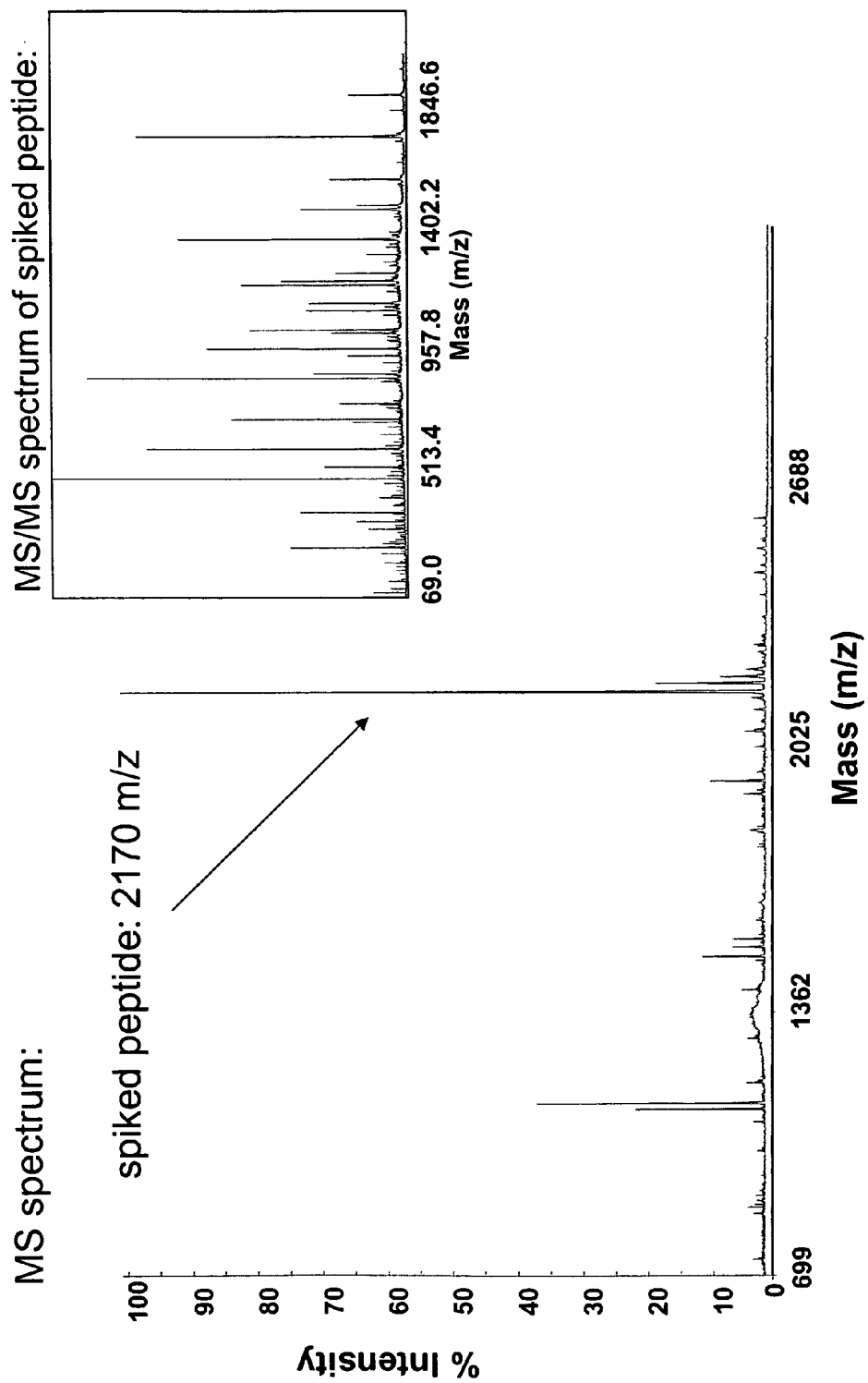
FIG. 4 shows an example of spiking of an isotope-labeled peptide VVGVPYQGDATALFILPSEGK (SEQ ID NO:1). The underlined Phe is the heavy isotopic labeled amino acid, and this synthetic standard peptide is 9 mass units heavier than its native peptide pair from the biological sample due the use of $^{13}C$ F during the peptide synthesis procedure. Shown is a MS spectrum, with the spiked peptide indicated. Also shown is a MSMS spectrum of the spiked peptide.

About 50 tryptic peptides representative of serum proteins were selected and synthesized as heavy isotopic forms. A serum sample was digested with trypsin, and the isotopically labeled peptides were spiked into the digested sample (see FIG. 2). The peptides were separated by reverse phase HPLC and deposited on a MALDI sample plate. The peptides were analyzed by MS and MS/MS to quantify and identify the peptides. The peptide ratio of test peptides to spiked heavy peptides was determined by LC-MALDI-TOF/TOF (see FIG. 3), and the selected peptides were identified by MS/MS (FIG. 4).

EXAMPLE 2

Generating Antibodies for Selected Peptides

The selected synthetic peptides are conjugated to KLH (keyhole limpet hemocyanin) and injected into rabbits. Test bleeds are collected and characterized by ELISA on the peptide antigen.

Once rabbits start to show high specific titers, 40 ml production bleeds are obtained. Bleeds are dialyzed overnight in 0.025M NaAcetate, 0.01M NaCl, pH 5.2, at 4° C., then spun at 10,000 rpm at 4° C. for 30 min to precipitate serum lipids. Serum supernatant is then purified by Protein A chromatography to isolate the IgG antibody fraction. Affinity chromatography is then performed using peptide antigen coupled to amino resin from Pierce (Rockford Ill.), coupling according to the manufacturer's directions. Protein A eluate is incubated with peptide antigen resin by rotation in a sealed column at room temperature for one hour. This column is drained, washed twice with PBS, and specific antibodies are eluted with 0.1M glycine, pH 2.7, and pooled fractions neutralized with 1M Tris-HCl, pH 9.5. The eluted specific antibody is then dialyzed overnight in PBS at 4° C.

EXAMPLE 3

Generating Aptamers for Selected Peptides

An aptamer library is synthesized using well known methods (Tuerk and Gold, *Science* 249:505-510 (1990); Ellington and Szostak, *Nature* 346:818-822 (1990); Joyce, *Curr. Opin. Struct. Biol.* 4:331-336 (1994); Gold et al., *Annu. Rev. Biochem.* 64:763-797 (1995); Jayasena, *Clin. Chem.* 45:1628-1650 (1999); Famulok and Mayer, *Curr. Top. Microbiol. Immunol.* 243:123-136 (1999)). The aptamer library is screened for binding to the peptides representative of serum proteins. Alternatively, antibodies to each of the selected peptides is generated. The aptamer or antibody binding agents are bound to a MALDI plate in a microarray format.

Aptamers specific to proteins/peptides present in a target sample are selected by differential screening of an aptamer library using proteins from a target sample and control sample. In this case, peptides are captured by the target sample specific aptamers and identified by mass spectrometry. The heavy isotope form of the identified peptides are synthesized and spiked in the peptides from biological samples with the same cleavage method for quantification and identification. The screening of aptamers and protein/peptides specific to target samples can be performed using steps similar to the following (see FIG. 5):

1. Select nucleotide library using proteins/peptides from target protein sample and elute the nucleotides that bind proteins in target sample after washing off the non-specific nucleotides.
2. The eluted nucleotides selected by target sample are hybridized to control sample to subtract aptamers that also bind to proteins/peptides in control sample.
3. The specific nucleotides to target sample are amplified and sequenced.
4. Proteins/peptides from target and control samples are labeled with fluorescent tags or mass tags and combined.
5. Individual aptamers on solid support are incubated with a binding solution containing labeled proteins or peptides from target or control samples simultaneously. Specific proteins/peptides are captured by their specific aptamers.
6. The specific captured proteins/peptides are quantified.
7. Aptmers that differentially detect proteins/peptides in target mixture are identified.
8. Proteins/peptides bound to the identified aptamers from step 7 are identified by tandem mass spectrometry.
9. The identified proteins/peptides are synthesized and labeled isotopically as standards.
10. The standard proteins/peptides are spiked to the control and target samples and captured by aptamers on microarray.
11. The peptides are quantified and identified by mass spectrometry.

EXAMPLE 4

Affinity Capture of Peptides by Microarray and Peptide Analysis by Mass Spectrometry Briefly, a tryptic digest of a serum sample is spiked with a known amount of heavy isotope labeled peptides, as described above. The spiked sample containing test sample peptides digested with trypsin and heavy isotopically labeled standard peptides are bound to the microarray containing binding agents. Unbound material is removed, and the microarray is washed to remove non-specifically bound material. The bound test peptides and standard peptides are analyzed by MS as described above. The ratio of test peptide and standard peptide is determined to quantify the amount of test peptide in the biological sample.

In more detail, a MALDI target surface is activated with neutravidin. The surface of a MALDI target is treated to bind biotinylated affinity reagent using the method described previously (Koopmann and Blackburn, *Rapid Commun. Mass Spectrom.* 455-462 (2003)) by sequentially incubating with polymer PEG-PLL-biotin and neutravidin for 1 h at room temperature in a humid chamber. The MALDI target is then washed and dried under nitrogen. The surface is ready to be used as a highly specific affinity capture device for biotinylated affinity reagents specific to selected peptides, such as antibodies and aptamers.

Biotinylation of antibodies and aptamers: Antibodies can be biotinylated through conjugation of carbohydrate to hydrazide with biotin. The aptamers can be biotinylated during the aptamer synthesis using a biotinylated nucleotide at the 5' end.

Array antibodies or aptamers on PLL-PEG-biotin neutravidin treated surface on a MALDI target: 10 fmole of biotinylated antibodies or aptamers are arrayed on the neutravidin coated MALDI target and incubated for a period of 2 h on the MALDI target in a humid chamber to prevent drying. The MALDI target is then dried under nitrogen.

Affinity capture of selected peptides on the MALDI-target surface: A tryptic digest of a serum sample is spiked with a known amount of heavy isotope labeled peptides, as described above. The prepared peptide mixture is incubated with microarray on a MALDI target for 2 h in PBS buffer, followed by two washes with PBS to remove the unbound material, drying and overlaying the sample with MALDI matrix.

The bound test peptides and standard peptides are analyzed by MS as described above. The ratio of test peptide and standard peptide is determined to quantify the amount of test peptide in the biological sample.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of detecting and quantifying polypeptides in a sample, comprising:
   (a) identifying a set of peptides corresponding to polypeptides of interest in a sample;
   (b) chemically synthesizing said set of peptides;
   (c) synthesizing isotopically labeled forms of said set of peptides to generate peptide standards;
   (d) generating a plurality of binding agents for said set of peptides;
   (e) immobilizing said plurality of binding agents to a solid support in an array format;
   (f) cleaving polypeptides in a test sample to generate cleaved test sample peptides corresponding to said peptide standards;
   (g) adding a predetermined amount of said peptide standards to said cleaved test sample;
   (h) contacting said cleaved test sample containing peptide standards with said array of immobilized binding agents;
   (i) washing said array to remove unbound peptides, thereby retaining affinity captured peptides comprising cleaved test sample peptides and standard peptides;
   (j) detecting the presence of said affinity captured peptides using mass spectrometry; and
   (k) quantifying the amount of said test sample peptides by determining the ratio of cleaved test sample peptides to corresponding standard peptides.

2. The method of claim 1, wherein the test polypeptides are cleaved with a protease.

3. The method of claim 2, wherein the protease is trypsin.

4. The method of claim 1, wherein said binding agent is an aptamer.

5. The method of claim 1, wherein said binding agent is an antibody.

6. A method of detecting and quantifying polypeptides in a sample, comprising:
   (a) generating a set of peptide standards by chemical synthesis;
   (b) isotopically labeling said set of peptide standards;
   (c) cleaving polypeptides in a test sample to generate cleaved test sample peptides;
   (d) adding a predetermined amount of said isotopically labeled peptide standards to said cleaved test sample, wherein said peptide standards correspond to peptides cleaved with the same reagent used to cleave the test sample;
   (e) contacting said cleaved test sample containing peptide standards with an array of immobilized binding agents specific for said peptide standards;
   (f) washing said array to remove unbound peptides, thereby retaining affinity captured peptides comprising cleaved test sample peptides and standard peptides; and
   (g) detecting the presence of said affinity captured peptides using mass spectrometry
   (h) quantifying the amount of said test sample peptides by determining the ratio of cleaved test sample peptides to corresponding standard peptides.

7. The method of claim 6, wherein the test polypeptides are cleaved with a protease.

8. The method of claim 7, wherein the protease is trypsin.

9. The method of claim 6, wherein said binding agent is an aptamer.

10. The method of claim 6, wherein said binding agent is an antibody.

11. A method of detecting and quantifying polypeptides in a sample, comprising:
    (a) generating a set of peptide standards by chemical synthesis;
    (b) isotopically labeling said set of peptide standards;
    (c) cleaving polypeptides in a test sample with trypsin to generate cleaved test sample peptides;
    (d) adding a predetermined amount of said isotopically labeled peptide standards to said cleaved test sample, wherein said peptide standards correspond to tryptic peptides;
    (e) contacting said cleaved test sample containing peptide standards with an array of immobilized binding agents specific for said peptide standards;
    (f) washing said array to remove unbound peptides, thereby retaining affinity captured peptides comprising cleaved test sample peptides and standard peptides; and
    (g) detecting the presence of said affinity captured peptides using mass spectrometry (h) quantifying the amount of said test sample peptides by determining the ratio of cleaved test sample peptides to corresponding standard peptides.

12. The method of claim 11, wherein said binding agent is an aptamer.

13. The method of claim 11, wherein said binding agent is an antibody.

14. The method of claim 1, wherein said peptide standards are labeled with a stable isotope.

15. The method of claim 6, wherein said peptide standards are labeled with a stable isotope.

16. The method of claim 11, wherein said peptide standards are labeled with a stable isotope.

17. The method of claim 1, wherein said isotopically labeled forms of said peptide standards are generated as said set of peptides is chemically synthesized.

18. The method of claim 1, wherein said isotopically labeled forms of said peptide standards are generated after said set of peptides is chemically synthesized.

19. The method of claim 6, wherein said isotopically labeled forms of said peptide standards are generated as said set of peptides is chemically synthesized.

20. The method of claim 6, wherein said isotopically labeled forms of said peptide standards are generated after said set of peptides is chemically synthesized.

21. The method of claim 11, wherein said isotopically labeled forms of said peptide standards are generated as said set of peptides is chemically synthesized.

22. The method of claim 11, wherein said isotopically labeled forms of said peptide standards are generated after said set of peptides is chemically synthesized.

23. A method of detecting and quantifying, polypeptides in a sample, comprising:
   (a) identifying a set of peptides corresponding to polypeptides of interest in a sample;
   (b) recombinantly expressing said set of peptides;
   (c) synthesizing isotopically labeled forms said set of peptides to generate peptide standards;
   (d) generating a plurality of binding agents for said set of peptides;
   (e) immobilizing said plurality of binding agents to a solid support in an array format;
   (f) cleaving polypeptides in a test sample to generate cleaved test sample peptides corresponding to said peptide standards;
   (g) adding a predetermined amount of said peptide standards to said cleaved test sample;
   (h) contacting said cleaved test sample containing peptide standards with said array of immobilized binding agents;
   (i) washing said array to remove unbound peptides, thereby retaining affinity captured peptides comprising cleaved test sample peptides and standard peptides;
   (j) detecting the presence of said affinity captured peptides using mass spectrometry; and
   (k) quantifying the amount of said test sample peptides by determining the ratio of cleaved test sample peptides to corresponding standard peptides.

24. The method of claim 23, wherein the test polypeptides are cleaved with a protease.

25. The method of claim 24, wherein the protease is trypsin.

26. The method of claim 23, wherein said binding agent is an aptamer.

27. The method of claim 23, wherein said binding agent is an antibody.

28. The method of claim 23, wherein said peptide standards are labeled with a stable isotope.

29. The method of claim 23, wherein said isotopically labeled forms of said peptide standards are generated as said set of peptides is recombinantly expressed.

30. The method of claim 23, wherein said isotopically labeled forms of said peptide standards are generated after said set of peptides is recombinantly expressed.

31. A method of detecting and quantifying polypeptides in a sample, comprising:
   (a) generating a set of peptide standards by recombinant expression;
   (b) isotopically labeling said set of peptide standards;
   (c) cleaving polypeptides in a test sample to generate cleaved test sample peptides;
   (d) adding a predetermined amount of said isotopically labeled peptide standards to said cleaved test sample, wherein said peptide standards correspond to peptides cleaved with the same reagent used to cleave the test sample;
   (e) contacting said cleaved test sample containing peptide standards with an array of immobilized binding agents specific for said peptide standards;
   (f) washing said array to remove unbound peptides, thereby retaining affinity captured peptides comprising cleaved test sample peptides and standard peptides; and
   (g) detecting the presence of said affinity captured peptides using mass spectrometry
   (h) quantifying the amount of said test sample peptides by determining the ratio of cleaved test sample peptides to corresponding standard peptides.

32. The method of claim 31, wherein the test polypeptides are cleaved with a protease.

33. The method of claim 32, wherein the protease is trypsin.

34. The method of claim 31, wherein said binding agent is an aptamer.

35. The method of claim 31, wherein said binding agent is an antibody.

36. The method of claim 31, wherein said peptide standards are labeled with a stable isotope.

37. The method of claim 31, wherein said isotopically labeled forms of said peptide standards are generated as said set of peptides is recombinantly expressed.

38. The method of claim 31, wherein said isotopically labeled forms of said peptide standards are generated after said set of peptides is recombinantly expressed.

39. A method of detecting and quantifying polypeptides in a sample, comprising:
   (a) generating a set of peptide standards by recombinant expression;
   (b) isotopically labeling said set of peptide standards;
   (c) cleaving polypeptides in a test sample with trypsin to generate cleaved test sample peptides;
   (d) adding a predetermined amount of isotopically labeled peptide standards to said cleaved test sample, wherein said peptide standards correspond to tryptic peptides;
   (e) contacting said cleaved test sample containing peptide standards with an array of immobilized binding agents specific for said peptide standards;
   (f) washing said array to remove unbound peptides, thereby retaining affinity captured peptides comprising cleaved test sample peptides and standard peptides; and
   (g) detecting the presence of said affinity captured peptides using mass spectrometry (h) quantifying the amount of said test sample peptides by determining the ratio of cleaved test sample peptides to corresponding standard peptides.

40. The method of claim 39, wherein said binding agent is an aptamer.

41. The method of claim 39, wherein said binding agent is an antibody.

42. The method of claim 39, wherein said peptide standards are labeled with a stable isotope.

43. The method of claim 39, wherein said isotopically labeled forms of said peptide standards are generated as said set of peptides is recombinantly expressed.

44. The method of claim 39, wherein said isotopically labeled forms of said peptide standards are generated after said set of peptides is recombinantly expressed.

* * * * *